United States Patent [19]

Schaaf et al.

[11] 4,177,205

[45] Dec. 4, 1979

[54] PROCESS FOR THE PREPARATION OF HIGHLY STABLE LIQUID CARBODIIMIDE-CONTAINING POLYISOCYANATE COMPOSITIONS

[75] Inventors: Robert L. Schaaf, Wyandotte; Peter T. Kan, Plymouth; Moses Cenker, Trenton, all of Mich.

[73] Assignee: BASF Wyandotte Corporation, Wyandotte, Mich.

[21] Appl. No.: 962,232

[22] Filed: Nov. 20, 1978

[51] Int. Cl.$^2$ .......................................... C07C 119/055
[52] U.S. Cl. ...................... 260/453 AM; 260/453 SP; 560/26; 521/901
[58] Field of Search ................. 260/453 AM, 453 SP, 260/566 R; 521/901

[56] References Cited

U.S. PATENT DOCUMENTS 3,761,502  9/1973  Kan et al. .......................... 260/453 P

*Primary Examiner*—Dolph H. Torrence
*Attorney, Agent, or Firm*—Joseph D. Michaels; Bernhard R. Swick; Robert E. Dunn

[57] ABSTRACT

Highly stable liquid 4,4'-diphenylmethane diisocyanate (MDI) containing MDI-carbodiimide adducts are prepared by (a) heating MDI at a temperature of from 60° C. to 120° C. for a period of from one hour to ten hours in the presence of tris(chloromethyl)phosphine oxide, (b) stopping the carbodiimide formation by adding thereto a quenchant selected from the group consisting of magnesium chloride hydrate, stannous chloride and trichlorosilane, (c) heating the reaction mixture at a temperature between 60° C. and 120° C. for a period of from 0.5 hour to 6.0 hours, and (d) cooling to room temperature. The resulting compositions are highly stable and may be advantageously employed in the preparation of polyurethane compositions.

7 Claims, No Drawings

PROCESS FOR THE PREPARATION OF HIGHLY STABLE LIQUID CARBODIIMIDE-CONTAINING POLYISOCYANATE COMPOSITIONS

BACKGROUND OF THE INVENTION

1. Field of the Invention

The present invention relates to a low temperature process for the preparation of liquid polyisocyanate compositions having enhanced stability. More particularly, the invention relates to liquid polyisocyanates obtained by heating 4,4'-diphenylmethane diisocyanate (MDI) or mixtures containing MDI at a temperature between 60° C. to 120° C. in the presence of tris(chloromethyl)phosphine oxide and thereafter stopping the carbodiimide formation by addition of certain quenchants.

2. Prior Art

The preparation of liquid carbodiimide-containing organic polyisocyanates by heating an organic polyisocyanate in the presence of catalytic amounts of tris(chloromethyl)phosphine oxide at a temperature of up to 120° C. is taught in U.S. Pat. No. 3,761,502. Disclosed in this patent is the fact that use of this catalyst provides an improvement over prior art processes since its reactivity is such that it is possible to control the carbodiimide formation thereby enabling the preparation of liquid compositions having controlled amounts of carbodiimide linkages. One of the problems encountered in following the process of this patent is that the resulting compositions are not stable and over a period of time show decreasing amounts of isocyanate content. The present invention is directed to an improved process for the preparation of liquid carbodiimide-containing MDI employing tris(chloromethyl)phosphine oxide as the carbodiimide-promoting compound.

SUMMARY OF THE INVENTION

The present invention relates to the preparation of highly stable liquid carbodiimide-containing MDI having an isocyanate content of from 20 to 32 percent by weight by (a) heating MDI at a temperature of from 60° C. to 120° C. for a period of from one hour to ten hours in the presence of tris(chloromethyl)phosphine oxide, (b) stopping the carbodiimide formation by adding thereto a quenchant selected from the group consisting of magnesium chloride hydrate, stannous chloride and trichlorosilane, (c) heating the reaction mixture at a temperature between 60° C. to 120° C. for a period of from 0 hour to 6.0 hours, and (d) cooling to room temperature. The resulting compositions are highly stable and may be advantageously employed in the preparation of polyurethane compositions.

DESCRIPTION OF THE PREFERRED EMBODIMENTS

In accordance with the subject invention, MDI or mixtures containing MDI are first subjected to treatment with a catalytic amount of tris(chloromethyl)phosphine oxide for a period of from one hour to ten hours at a temperature of from 60° C. to 120° C. Thereafter, the reaction mixture is treated with a quenchant, namely, a magnesium chloride hydrate, stannous chloride or trichlorosilane to stop the catalyst action. The mixture may then be heated to acquire complete combination of catalyst and quenchant. It has been found that only these compounds, of a large number of candidate quenchants, were effective in stopping the carbodiimide formation. The amount of quenchant employed in the process of the subject invention will generally be from 1.0 mole to 3.0 moles per mole of catalyst. After the quenchant is added to the reaction mixture, the mixture is maintained at a temperature between 60° C. and 120° C. for a period of from 0 hour to 6.0 hours, preferably from 2 to 4 hours, and thereafter cooled to room temperature.

While pure MDI is the polyisocyanate of choice in the process of the subject invention, mixtures containing MDI may also be employed. These mixtures are generally prepared by condensing aniline with formaldehyde to form a mixture of amines which is subsequently phosgenated to produce the corresponding isocyanates. These amine mixtures generally contain from 75 to 25 weight percent of diamines of which from one percent to thirty percent is the 2,4'-isomer, and less than one percent to ten percent is the 2,2'-isomer, and from 25 percent to 75 percent of higher functional diphenylmethane bases.

The catalyst employed in the process of the subject invention is tris(chloromethyl)phosphine oxide. This compound is well known in the art and may be prepared in the manner set forth in U.S. Pat. No. 3,761,502. The catalyst is generally employed in an amount ranging from 0.05 part to 1.0 part, preferably from 0.1 to 0.5 part by weight per 100 parts by weight of MDI. The time required for carrying out the reaction may vary from one hour to ten hours, preferably from two to six hours.

In a preferred embodiment of the subject invention, the liquid carbodiimide-containing polyisocyanates are prepared in the presence of a polyol resulting in liquid urethane-modified carbodiimide-containing polyisocyanates. Any of the polyols also known as active hydrogen-containing compounds which are well known in the art may be employed. Further details of these compounds can be found in U.S. Pat. No. 3,761,502.

In the Examples that follow, all parts are by weight unless otherwise indicated. The physical properties of the foams were determined in accordance with the following ASTM tests:
Density—D-1622-63
Tensile Strength—D-1623-72
Elongation—D-412
Split Tear—D-470
Graves Tear—D-624
Shore "D" Hardness—D-676
Flex Recovery—D-1623-72
Flex Modulus—D-1623-72

EXAMPLES I-XII

A series of experiments was conducted employing a reactor equipped with a stirrer, thermometer, condenser, inlet and outlet means and heat exchange means. The reactor was heated to 50° C., flushed with nitrogen and while maintaining a blanket of nitrogen, 250 parts of molten 4,4'-diphenylmethane diisocyanate and 0.39 part (0.16 percent) of tris(chloromethyl)phosphine oxide were added thereto. The temperature was raised to 100° C. while stirring the reaction mixture. The reaction mixture was maintained at 100° C. until the isocyanate content decreased to about 30.4 percent (2.5 hours). At this time, various candidate quenchants in differing amounts were added to the reaction mixture. Heating continued at 100° C. and the isocyanate content of the product was measured over a period of hours. Details of the preparations are presented in Table I. As the data indicate, only certain compounds were effective quenchants. Closely related compounds, i.e., calcium chloride hydrate and ferrous chloride were not useful in the process of the subject invention.

Table I

| Example | Quenchant | Ratio* | % NCO at x hrs. After Addition of Quenchant | | | |
|---|---|---|---|---|---|---|
| | | | 0 | 1 | 2 | 3 |
| I | $MgCl_2 \cdot 2H_2O$ | 1:1 | 30.4 | 30.1 | 29.9 | 29.9 |
| II | $MgCl_2 \cdot 2H_2O$ | 2:1 | 30.4 | 29.8 | 29.6 | 29.5 |
| III | $MgCl_2 \cdot 6H_2O$ | 2:1 | 30.4 | 29.3 | 28.9 | 28.6 |
| IV | $MgCl_2 \cdot H_2O$ | 1:1 | 30.3 | 30.0 | 29.9 | 29.7 |
| V | $BaCl_2 \cdot 2H_2O$ | 2:1 | 30.1 | 29.1 | 28.2 | 27.4 |
| VI | $CaCl_2 \cdot 2H_2O$ | 2:1 | 30.4 | 29.4 | 28.6 | 27.9 |
| VII | $FeCl_2$ | 2:1 | 30.3 | 29.6 | 28.5 | 27.9 |
| VIII | $SnCl_2$ | 2:1 | 30.3 | 29.8 | 29.7 | 29.4 |
| IX | $MnCl_2$ | 2:1 | 30.5 | 29.7 | 28.7 | 28.1 |
| X | $HSiCl_3$ | 2:1 | 30.5 | 30.3 | 30.4 | 30.3 |
| XI | $HSiCl_3$ | 1:1 | 30.6 | 30.3 | 30.0 | 30.3 |
| XII | $CH_3SiCl_3$ | 2:1 | 30.3 | 29.5 | 28.9 | 28.0 |

*Mole ratio Quenchant to Catalyst

EXAMPLES XIII-XX

Tests were carried out on the liquid carbodiimide-containing polyisocyanate compositions which were prepared in accordance with the subject invention to illustrate their stability over a period of months. As a control, a product prepared in accordance with the process described in U.S. Pat. No. 3,761,502 was used. Details of the preparations and stability tests are presented in Table II below.

Table II

| Example | Temp. °C. | $(ClCH_2)_3PO$ Wt. % | Heating Time, hrs. Before Quench | Heating Time, hrs. After Quench | Quenchant | Mole* Ratio | % NCO After x Months at Room Temperature | | | |
|---|---|---|---|---|---|---|---|---|---|---|
| | | | | | | | 1 | 2 | 3 | 4 |
| XIII | 100 | 0.16 | 3.0 | 2 | $MgCl_2 \cdot 2H_2O$ | 2:1 | 29.2 | 29.0 | 29.1 | N.D. |
| XIV | 100 | 0.16 | 2.5 | 4 | $MgCl_2 \cdot 6H_2O$ | 2:1 | 27.9 | 27.8 | 27.5 | 27.5 |
| XV | 80 | 0.40 | 4.0 | 2 | $MgCl_2 \cdot 2H_2O$ | 2:1 | 28.4 | 28.2 | 28.1 | N.D. |
| XVI | 80 | 0.40 | 3.5 | 2 | $MgCl_2 \cdot 2H_2O$ | 1:1 | 29.3 | 29.1 | 28.9 | N.D. |
| XVII | 80 | 0.40 | 4.5 | 4 | $HSiCl_3$ | 1.5:1 | 28.9 | 28.8 | 28.4 | 28.2 |
| XVIII | 100 | 0.16 | 3.5 | 4 | $HSiCl_3$ | 1:1 | 29.0 | 28.7 | 28.3 | 27.7 |
| XIX | 100 | 0.16 | 2.5 | 3 | $HSiCl_3$ | 2:1 | 30.0 | 29.7 | 29.5 | 29.1 |
| XX | 120 | 0.06 | 3.5 | 0 | $SnCl_2$ | 1:1 | 29.6 | 29.1 | 28.7 | 28.6 |
| Control | 100 | 0.16 | 3.5 | — | None | — | 27.2 | 25.4 | N.D. | N.D. |
| Control | 80 | 0.40 | 4.5 | — | None | — | 25.1 | N.D. | N.D. | N.D. |

N.D. - not determined
*Quenchant to Catalyst

EXAMPLE XXI

A reactor equipped as described in Example I was charged with 250 parts of 4,4'-diphenylmethane diisocyanate and heated to 65° C. under a slow stream of nitrogen. Thereafter, 30 parts of a 2000 molecular weight polyoxypropylene glycol was added to the reactor and the mixture was stirred at 80° C. for one hour. The reaction mixture was then heated to 100° C. and treated with 0.39 part of tris(chloromethyl)phosphine oxide. After heating at 100° C. for 2.5 hours, the isocyanate content of the prepolymer was determined to be 27.0 percent by weight. At this time, 0.52 part of magnesium chloride dihydrate was added and the mixture was heated for two hours at 100° C. and thereafter cooled to room temperature. Analysis of the product showed a 25.7 percent by weight isocyanate content.

EXAMPLE XXII

A microcellular foam was prepared employing as the isocyanate component, the product of Example XIII(65.1 parts, 105 Index). The polyol employed was a 6800 molecular weight polyol prepared by capping with ethylene oxide a propylene oxide adduct of trimethylolpropane, said polyol having an oxyethylene content of 15 percent by weight of the polyol (100 parts). In addition, 20 parts of 1,4-butanediol, 2.0 parts of triethylene diamine and 0.02 part of dibutyltindilaurate were employed. The physical properties of the resulting foam are as follows:

| Density, pcf. | 59.0 |
|---|---|
| Tensile strength, psi. | 1584 |
| Elongation, percent | 90 |
| Split Tear, pi. | 80 |
| Graves Tear, pi. | 215 |
| Shore "D" Hardness | 46–40 |
| Flex. Recovery | 5/2 |
| Heat Sag @ 250° F. | 0.28 |
| Flexural Modulus, psi. at 72° F. | 12170 |

The embodiments of the invention in which an exclusive property or privilege is claimed are defined as follows:

1. A process for the preparation of highly stable liquid carbodiimide-containing 4,4'-diphenylmethane diisocyanate having an isocyanate content of from 20 to 32 percent by weight comprising
   (a) heating 4,4'-diphenylmethane diisocyanate or mixtures containing same at a temperature of from 60° C. to 120° C. for a period of from one hour to ten hours in the presence of tris(chloromethyl)phosphine oxide,
   (b) stopping the carbodiimide formation by adding to the reaction mixture a quenchant selected from the group consisting of magnesium chloride hydrate, stannous chloride and trichlorosilane,
   (c) maintaining the reaction mixture at a temperature of from 60° C. to 120° C. for a period of from 0 hour to six hours and
   (d) cooling the product resulting from (c) to room temperature.

2. The process of claim 1 wherein the quenchant is stannous chloride.

3. The process of claim 1 wherein the quenchant is magnesium chloride hydrate.

4. The process of claim 1 wherein (a) is conducted at a temperature of from 80° C. to 100° C. for a period of from two to six hours.

5. The process of claim 1 wherein the quenchant is employed in a mole ratio of quenchant to catalyst of from 1:1 to 3:1.

6. The process of claim 1 wherein (a) is carried out in the presence of a polyol.

7. A highly stable liquid composition prepared in accordance with claim 1 or 6.

* * * * *